(12) United States Patent
Duesberg et al.

(10) Patent No.: US 9,453,811 B2
(45) Date of Patent: Sep. 27, 2016

(54) ASYMMETRIC BOTTOM CONTACTED DEVICE

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

(72) Inventors: Georg Stefan Duesberg, Dublin (IE); Hye-Young Kim, Dublin (IE)

(73) Assignee: THE PROVOST, FELLOWS, FOUNDATION SCHOLARS, AND THE OTHER MEMBERS OF BOARD OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 14/084,959

(22) Filed: Nov. 20, 2013

(65) Prior Publication Data

US 2014/0151631 A1 Jun. 5, 2014

(30) Foreign Application Priority Data

Nov. 20, 2012 (GB) .................................. 1220804.7

(51) Int. Cl.
*G01N 27/403* (2006.01)
*G01N 27/12* (2006.01)

(52) U.S. Cl.
CPC .................................. *G01N 27/129* (2013.01)

(58) Field of Classification Search
CPC ........... G01N 27/414; G01N 27/4145; G01N 27/4162; G01N 27/4161
USPC .............................................. 257/9, 252, 253
See application file for complete search history.

(56) References Cited

U.S. PATENT DOCUMENTS

2009/0084678 A1* 4/2009 Joshi et al. .............. 204/403.14

OTHER PUBLICATIONS

Chen et al., "Graphene-Silicon Schottky Diodes", Nano Letters 11(5):5097 (2011).
Chen et al., "Oxygen sensors made by monolayer graphene under room temperature", Applied Physics Letters 99:243502(1-3) (2011).
Cheung et al., "Extraction of Schottky diode parameters from forward current-voltage characteristics", Appl. Phys. Lett, 49(2):85-87 (1986).

(Continued)

*Primary Examiner* — Tan N Tran
(74) *Attorney, Agent, or Firm* — David S. Resnick; Nixon Peabody LLP

(57) ABSTRACT

The invention provides a Bottom Contacted 2D-layer Device (BCD) for the determination of graphene doping and chemical sensing. The device can be made by transfer of high quality CVD grown graphene films onto n- or p-doped silicon substrates yielding Schottky barrier diodes. Exposure to liquids and gases change the charge carrier density in the graphene and as a result the electrical transport of the device is modulated. The changes can be easily detected and interpreted in the doping power of the adsorbent. This principle allows one to create a new type of chemical sensor platform exploiting the monolayer nature of graphene or other carbon material. The device benefits from facile fabrication and the result is a robust device which can investigate surface chemistry on monolayer materials.

22 Claims, 14 Drawing Sheets

(56) References Cited

OTHER PUBLICATIONS

Daly et al., "Cell Proliferation Tracking Using Graphene Sensor Arrays", Journal of Sensors, 2012:1-7 (2012).
Das et al., "Changes in the electronic structure and properties of graphene induced by molecular charge-transfer", Chem, Comm 41:5155-5157 (2008).
Dong et al., "Doping Single-Layer Graphene with Aromatic Molecules", Small 5(12):1422-1426 (2009).
Kauffman et al., "Graphene versus carbon nanotubes for chemical sensor and fuel cell applications", Analyst 135 (11):1190-2797 (2010).
Keffous of al., "Effect of series resistance on the performance of high resistivity silicon Schottky diode", Applied Surface Science 218:336-342 (2003).
Kong et al., "Nanotube Molecular Wires as Chemical Sensors", Science 287(5453):622-625 (2000).
Kumar et al., "CVD growth and processing of graphene for electronic applications", Phys. Status Solidi B 248 (11):2604-2608 (2011).
Miao et al., "High Efficiency Graphene Solar Cells by Chemical Doping", Nano Letters 12(6):2745-2750 (2012).
Neto et al., "The electronic properties of graphene", Reviews of Modern Physics 81(1):109-162 (2009).
Novoselov et al., "Two-dimensional gas of massless Dirac fermions in graphene", Nature 438(7065):197-200 (2005).
Schedin et al., "Detection of individual gas molecules adsorbed on graphene", Nature Materials 6(9):652-655 (2007).
Shin et al., "Tailoring Electronic Structures of Carbon Nanotubes by Solvent with Electron-Donating and -Withdrawing Groups", J. Am. Chem. Soc 130(6):2062-2066 (2008).
Tongay et al., "Tuning Schottky diodes at the many-layer-graphene/semiconductor interface by doping", Carbon 49:2033-2038 (2011).
Tung, "Electron transport at metal-semiconductor interfaces: General theory", Physical Review B Condens Matter 45 (23):13509-13523 (1992).
Xia et al., "Graphene Field-Effect Transistors with High On/Off Current Ratio and Large Transport Band Gap at Room Temperature", Nano Letters 10(2):715-718 (2010).
Yang et al., "Graphene Barristor, a Triode Device with a Gate-Controlled Schottky Barrier", Science 336 (6085):1140-1143 (2012).
Yavari et al., "Graphene-Based Chemical Sensors", J. Phys. Chem. Lett. 3(13):1746-1753 (2012).
Yim et al., "Carbon-Silicon Schottky Barrier Diodes", Small 8(9):1360-1364 (2012).
Zhang et al., "Opening an Electrical Band Gap of Bilayer Graphene with Molecular Doping", ACS Nano 5 (9):7517-7524 (2011).

\* cited by examiner

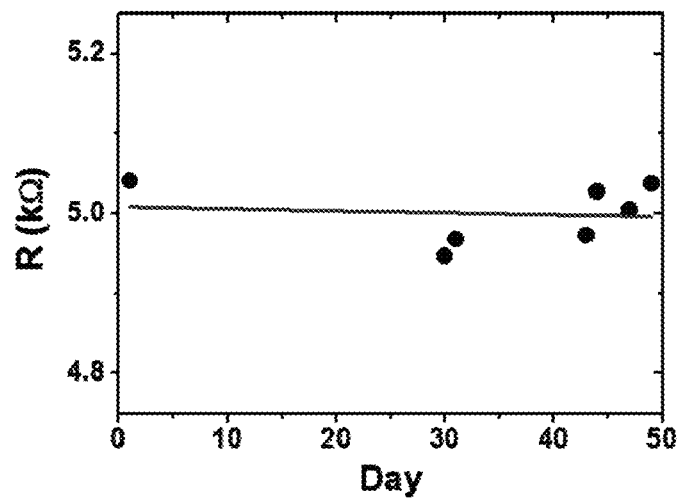
FIG. 7A
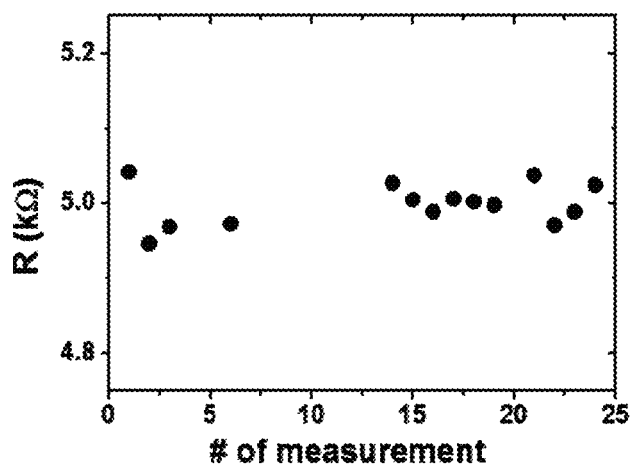
FIG. 7B
| Day | 1 | 30 | 31 | 43 | 44 | 47 | 49 |
|---|---|---|---|---|---|---|---|
| η | 1.40 | 1.41 | 1.41 | 1.40 | 1.41 | 1.41 | 1.42 |
FIG. 7C

ASYMMETRIC BOTTOM CONTACTED DEVICE

CROSS-REFERENCE TO RELATED APPLICATION

This application claims benefit of Great Britain Application No. 1220804.7 filed Nov. 20, 2012, the contents of which are incorporated herein by reference in its entirety.

BACKGROUND

Graphene has attracted much excitement in academic and industrial research. Its 2D nature gives cause to unique electronic properties. The monolayer nature lets π-conjugated system entirely exposed to external influence of its surroundings. While this is a general problem in controlling its properties, doping of graphene is much sought for numerous electronic and photonic applications. Schedin et al *Nature Materials* 2007, 6, 652, showed in ultra high vacuum conditions that adsorption events of molecules to graphene changed its electronic properties. This finding led to intensive research on the chemical induced doping of graphene for numerous applications.

While for blockbuster applications such as displays permanent changes in the charge carrier density increases the conductivity the potential lies in opening up a band gap to create all carbon based electronics. For sensing changes the electronic properties are to be monitored electrically in chemical field effect transistors or chemical resistors (ChemFETs and chemiresistors) sensors.

There is a worldwide demand for sensors in particular for stand-alone and mobile systems for environmental, air quality and safety control. The most established techniques such as mass spectrometry, electrochemical, infrared or metal oxide sensors suffer either from limited sensitivity, high power consumption, high production cost or inability to miniaturise. These challenges can be overcome in chemiresistors where with the discovery of nanomaterials such as nanotubes and -wires which possess high surface-to-volume ratio detection levels of the order of ppm or sub-ppm have been reported, as disclosed in Kauffman, D. R.; Star, A. *Analyst* 2010, 135, 2790. This matches the sensitivity of conventional metal oxide film sensors at room-temperature, thereby avoiding energy intensive operation at elevated temperatures. However a problem exists over scalability and reproducibility of these devices.

A number of groups have shown graphene as sensors for gases and liquids. Besides having high sensitivity graphene is potentially easy to manufacture and chemically robust, however device reliability is heavily dependent on the quality of the graphene and selectivity hinges on contact engineering and passivation of the channel.

It is therefore an object to provide an improved sensor device to overcome at least one of the above mentioned problems.

SUMMARY

According to the invention there is provided a Bottom Contacted 2D-layer Device (BCD) for the determination of graphene doping and chemical sensing.

In one embodiment there is provided a device comprising:
an electrode;
a 2D material layer in lateral contact with the electrode, wherein the charge transport can be measured vertically.

In one embodiment the device can be prepared by transfer of high quality CVD grown graphene films onto n- or p-doped silicon substrates yielding Schottky barrier diodes. Exposure to liquids and gases change the charge carrier density in the graphene and as a result the electrical transport of the device is modulated. The changes can be easily detected and interpreted in the doping power of the adsorbent. This principle allows one to create a new type of chemical sensor platform exploiting the monolayer nature of graphene. The sensor device benefits from facile fabrication and embodies a robust device to investigate surface chemistry on monolayer materials.

In one embodiment there is provided a Bottom Contacted 2D-layer Devices (BCD), were the graphene is laterally in contact with p- or n-type Silicon graphene. With this diode type configuration it is possible to determine the change in the work function and doping of graphene upon exposure to gases, liquids and solids.

In one embodiment there is provided a variable barrier diode, called "barrister", in which the barrier height can be tuned by applying a gate voltage to the graphene. The BCDs showed high sensitivity towards liquid and gaseous electron donor and acceptor substances, such as anisole, benzene, chlorobenzene, nitrobenzene and gaseous ammonia. Careful analysis of the recorded data with an equivalent circuit model showed that the various adsorbents caused a variation of the Schottky barrier height ($\phi_B$) and the conductivity of the graphene. The data can be used to determine the doping power of various adsorbents and to their identification. This novel sensor design has the advantage of facile production and fully exploits the two dimensional nature of the graphene.

In one embodiment there is provided chemical or environmental sensing using 2D graphene as a sensing layer arranged in a Schottky diode type device.

In one embodiment there is provided a device which measures doping vertically e.g. directly from underneath. While prior methods use the conductivity along the graphene (ChemFet and Chemiresistor). The vertical measurement allows for the charge carriers, the doping and the quality of graphene can be determined more readily.

The sensing mechanism is due to the change of charge carries in 2D graphene flakes, measured due to the charge injection through an ohmic metal contact and a Schottky contact applied horizontally over an area of the 2D layer.

As the doping can be caused by adsorption of various molecules to the 2D layer the devices can be used as sensor. For example, but not limited, such a device enables direct label-free detection of receptor ligand interaction and the direct growth detection of cells residing on top of a buffer layer. Applications of the device can be used diagnostics, Q&S testing in industrial samples (quick test for contamination, for resistance, etc.).

The unique properties of graphene stem from the fact that carbon forms extremely stable conjugated bonds and that it is of 2D nature—an all surface material. Due to this fact the exposed pi-conjugated system can be altered easily, as it is exposed to the environment entirely. Thus these changes to the electronic system alter the electronic properties of the graphene. A sensor can be picked up electrically, which would a guarantee a simple label free sensor, in comparison to IR, Mechanical etc. systems. In comparison to MOx sensors the sensor devices of the invention work at room temperature.

In one embodiment the device comprises carbon (graphene, single layer, thin film of sp2 rich) carbon to form an interface a semiconductors. As a result, a Schottky barrier (SB) which can be used as diode devices is formed. The invention shows that the conduction through this diode is changed upon exposure of the graphene surface diode. Since the graphene is contacted laterally (bottom) cracks, impurities etc. do not change the performance of the devices.

In another embodiment there is provided A sensor device comprising:
 a semiconductor material;
 a 2D layer of carbon in lateral contact with the semiconductor material, wherein changes in the charge carriers in the carbon can be measured vertically to provide a sensor function.

BRIEF DESCRIPTION OF THE DRAWINGS

The invention will be more clearly understood from the following description of an embodiment thereof, given by way of example only, with reference to the accompanying drawings, in which:—

FIG. 7 illustrates (a) Stability of the graphene/n-Si SD device as a sensor over 49 days. The resistance value was extracted at 1 V bias voltage using diode model. (b) The measurement of repeatability characteristics of graphene/n-Si SD for sensing of various chemicals and recovered by a bake on a hotplate. (c) The variation of ideality factor as function of time;

DETAILED DESCRIPTION OF THE DRAWINGS

Monolayered (2D) structures, e.g. graphene, exhibit unique mechanical and electrical properties. As all surface materials their electronic properties are influenced by the chemical surroundings. This can lead to chemical sensing. Graphene has shown to show ultimate sensitivity being able to detect single molecules. The sensing mechanism is due to the change of charge carries in 2D graphene films.

Figure 1:
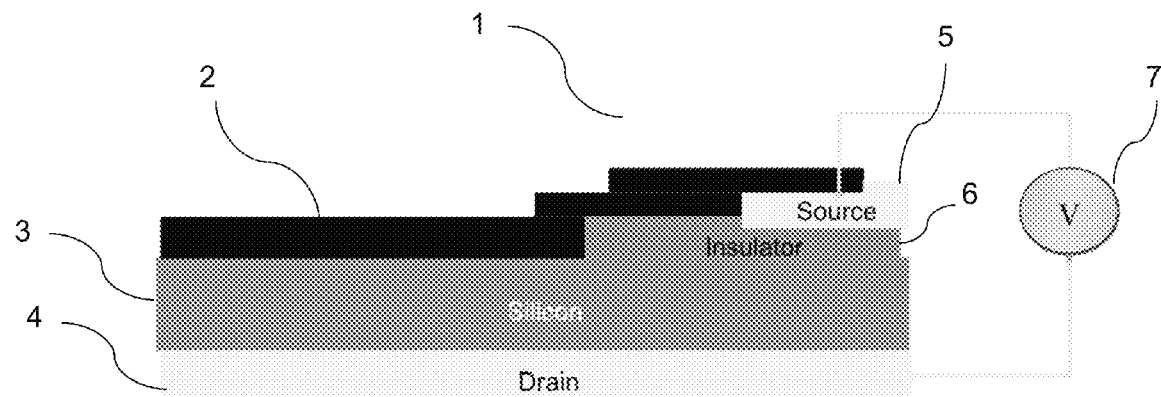
FIG. 1 illustrates a schematic of the device according to one embodiment.

FIG. 1 illustrates a schematic of the device according to one embodiment indicated generally by the reference numeral 1. A monolayered graphene material layer 2 is in contact with a semiconductor 3 (for example silicon) establishing a Schottky contact. A drain 4, a source 5, insulator 6 and power supply 7 is also provided to make up the Schottky contact. Upon exposure to analyte the SBD resistance is changed due to work function change in the monolayer, the operation and results of which are described in more detail below.

The graphene layer 2 can be synthesized by chemical vapor deposition (CVD) on copper (Cu) foils (Gould, 25 μm). Briefly, samples can be introduced into a quartz tube furnace and ramped to 1035 degC under $H_2$ flow (~0.2 Torr), and annealed for 20 minutes. The growth entailed a mixture of $CH_4$ (10 sccm) and $H_2$ (2.5 sccm) for 20 mins (Pressure ~0.07 Torr). After that the samples cooled to room temperature under $H_2$ flow. The graphene film was transferred by the conventional polymer supported transfer technique, whereby polymethyl methacrylate (PMMA, MicroChem) was spin-coated on graphene/Cu foil and the deposited carbon on back of Cu foil was mechanically removed and then placed in an etchant solution (Ammoniumpersulfate, APS 100). The Schottky contact was formed by transferring single layer graphene to n-type silicon (n-Si) and p-type silicon (p-Si) substrates with a doping density of $5 \times 10^{14}$ $cm^{-3}$ and $1.5 \times 10^{15}$ $cm^{-3}$.

Figure 2A:
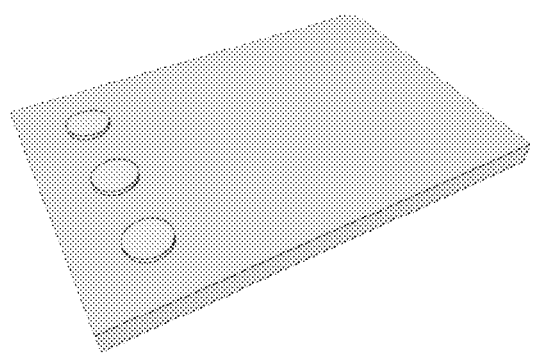
FIG. 2 illustrates a number of schematics of the fabrication process of graphene/n-Si SD where (a) The source electrode (Ti/Au=20/80 nm) is deposited immediately after removal of the native silicon oxide layer by immersion in 3% HF for 30 seconds. (b) Insulating material ($SiO_2$) with 150 nm is deposited to prevent electrical flow between the drain electrode and the substrate. (c) The drain electrode (Ti/Au=20/80 nm) is deposited. (d) Graphene is transferred after removal of the native oxide (1% HF for 1 minute). (e) Photograph of the device covered with chemical solution. (f) Representative Raman spectrum of transferred graphene on $SiO_2$ and on Si. The principal peaks observed in graphene are the D, G, and 2D-peaks at ~1340 $cm^{-1}$, 1590 $cm^{-1}$ and 2680 $cm^{-1}$, respectively. This shows that single layer graphene is transferred successfully to both $SiO_2$ and Si.
Figure 2B:
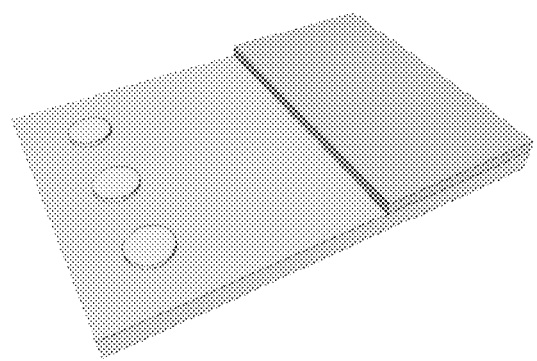
Figure 2C:
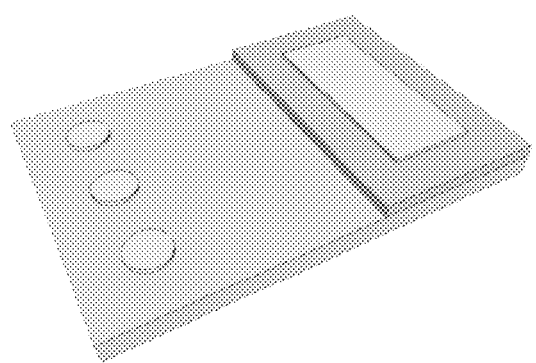
Figure 2D:
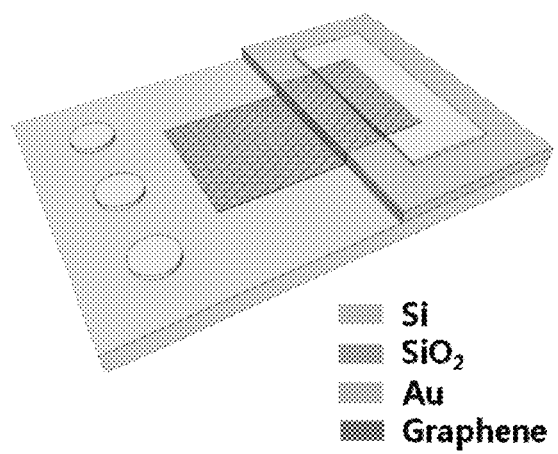

Referring to FIG. 2, in order to form an ohmic contact between source electrodes and silicon substrates, the native silicon oxide layer was removed by immersion in 3% diluted hydrofluoric acid (HF) for 30 seconds followed by deposition of titanium/gold (Ti/Au)=20/80 nm using a shadow mask with a radius of 1 mm (FIG. 2(a)), shown as three circles. The electrodes act as a source for the n-Si and drain for the p-Si device, respectively. Before the deposition of drain (source) electrodes, 150 nm of $SiO_2$ was deposited on the silicon substrate with metal shadow mask to prevent the direct current flow from source to drain electrodes (shown as layer on right hand side of FIG. 2(b)), followed by deposition of Ti/Au=20/80 nm (shown FIG. 1(c)). The graphene film was transferred on top of the $Si/SiO_2$/Ti/Au structure after an HF dip, and the PMMA layer was dissolved in warm acetone (FIG. 2 (d)). To perform chemical sensing, a solution drop with 60 μl was placed on top of graphene sheet as shown in FIG. 2(e). The measurement was done within 1 min and the sample was rinsed by IPA for 30 min. After rinsing the sample was annealed at 200° C. for 2 minutes to remove molecules from the graphene surface.

Electrical measurements of the device were performed with a Keithley model 2612A SourceMeter Unit in a Suess probe station in ambient environment and a custom-made gas sensing chamber. Raman spectrums were taken with a Witec Alpha 300 Raman microscope with a 532 nm excitation wavelength. The CVD growth yielded a continuous layer of mainly monolayer graphene of area of close to 1 cm². Careful transfer insured that the graphene layer connected the gold pad on the SiO2 insulator layer t the bare silicon, with touching the electrodes directly connected to the silicon layer, as indicated in FIG. 2 d. The graphene covered an area on the n-doped and xxx mm2 on the p-doped silicon substrate as determined by SEM. Raman spectroscopy was used to determine the quality of graphene.

FIG. 2(f) shows Raman spectra of graphene on $SiO_2$ and on Si. The principal peaks observed in graphene are G peak at 1590 $cm^{-1}$ and 2D peak at 2680 $cm^{-1}$. The peak ratio and width of the 2D peak indicate single layer graphene. A small D peak at 1340 $cm^{-1}$ highlights the presence of some defected carbon, which might also stem from the polymer residues.

Figure 3A:
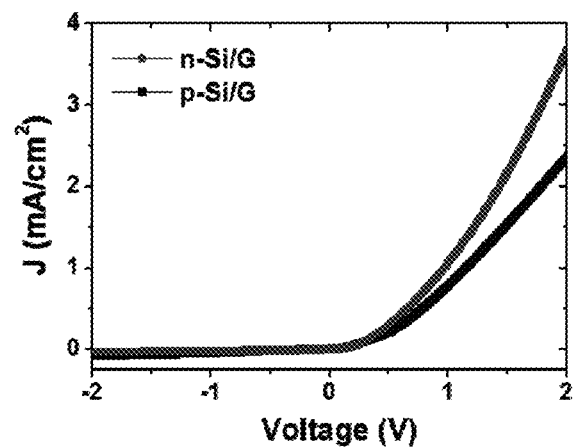
FIG. 3 illustrates (a) J-V characteristics of a pristine graphene/n-Si and graphene/p-Si SD. (b) A logarithmic J-V curve. (c) dV/dJ versus 1/J plot was extracted from the I-J curve according to the suggested equivalent circuit model at forward bias. The linear slope of the fitted line indicates the validity of the equivalent circuit model.
Figure 3B:
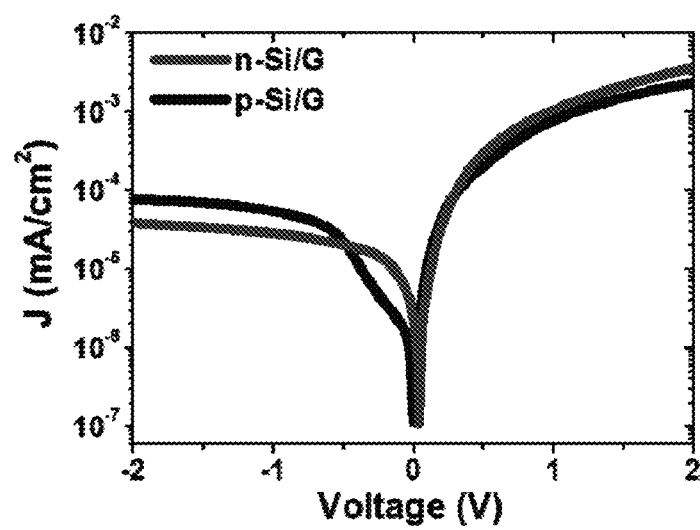
Figure 3C:
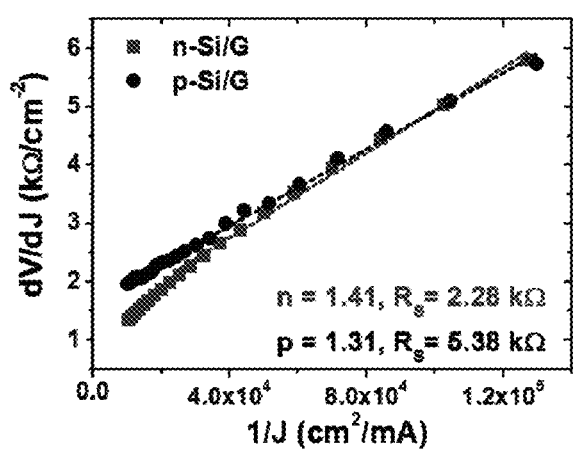

FIG. 3 (a) shows the current density-voltage (J-V) characteristics of the graphene on n-Si and p-Si device measured at room temperature with a voltage bias range of ±2 V. The drain and source electrode were positively and negatively charged to applied forward bias, respectively. The graphene is fully electrically intact and contacted by the gold pad, the graphene/silicon interface forms a Schottky barrier, which exhibits typical rectifying behaviour. The understanding of a Schottky diode are dominated by and its understanding is important for device applications. A SD can be described with on the thermionic emission theory in which the J-V relationship is given by Eq. (1):

$$J = J_s \left[ \exp\left(\frac{qV_D}{\eta k_B T}\right) - 1 \right] \quad (1)$$

where $\eta$ is the ideality factor, q is the electronic charge, $k_B$ is the Boltzmann constant, T is the absolute temperature, $V_D$ is the voltage applied across the junction and $I_s$ is the reserve saturation current. It can be expressed by Eq. (2):

$$J_s = A^* T^2 \exp\left(-\frac{q\phi_B}{k_B T}\right) \quad (2)$$

where A is the effective area of the diode contact, A* is the Richardson constant which is equal to 112 $Acm^{-2}K^{-2}$ for n-Si and 32 $Acm^{-2}K^{-2}$ for p-Si and $\phi_B$ is the Schottky barrier height of the diode. The ideality factor of a SD is a value of how closely the diodes follow the ideal behaviour on a logarithmic scale, with ideal being 1.

In practice there are second order effects giving raise to deviations from this simple description. This is visible in the high bias regime (FIG. 3 b) where the diode deviates from the initial linear behaviour. There are several reasons for this, including the resistance of the graphene and the silicon substrate, contact resistances of the source and drain electrodes, and interface states at the Schottky junction. These effects of the diode resistance $R_S$ is usually modelled with a series combination of a diode and a resistor. Essentially the diode can be described with the ideality factor $\eta$ and the resistance $R_S$ as shown in FIG. 3 (c). Following this $\phi_B$ is extracted using the Cheung's function, as disclosed in a paper by Cheung, S. K.; Cheung, N. W. *Applied Physics Letters* 1986, 49, 85. According to the model $\eta$ and $R_S$ of the graphene/n-Si SD is 1.41, 2.28 kΩ and of the graphene/p-Si SD is 1.31, 5.38 kΩ. The $\phi_B$ value was found to be 0.79 eV (n-Si) and 0.74 eV (p-Si).

The electronic structure of single wall carbon nanotubes gives rise to changes in their electrical properties and Raman spectra, similar phenomena has been reported for graphene. Because the injection of the majority carriers from graphene to semiconductor (silicon) is determined by the $\phi_B$, chemically modification of the graphene directly controls the current across the graphene/semiconductor interface.

Various electron-donors and acceptors can be applied to change the electron density of the graphene. Various solvents and solutions were directly applied onto the devices as shown in FIG. 2 (e), by simply using a pipette. The droplet volume was typically 60 µl-120 µl covering the entire graphene/Si area. The analytes were simply exchanged by rinsing the chip with solvent, blow-drying with nitrogen. This is repeated more than 20 times over a period of 49 days, as shown in FIG. 7. When the diode response was recovered to its pristine values a bake to 200° C. in ambient was applied. It has to be pointed out that these procedures were repeated up to 24 times, showing incredible stability of the device.

Figure 4A:
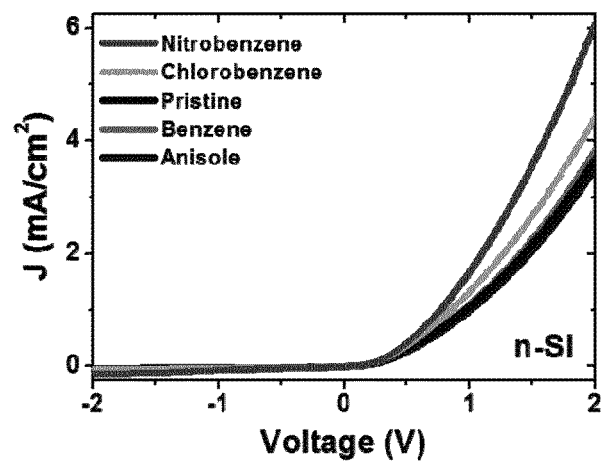
FIG. 4 illustrates a J-V characteristics with pristine and various aromatic molecules doped graphene on (a) n-Si, (b) p-Si. (c) Experimental variation of the series resistance ($R_S$) extracted from forward I-J curve, for graphene/n-Si and /p-Si Schottky diode.
Figure 4B:
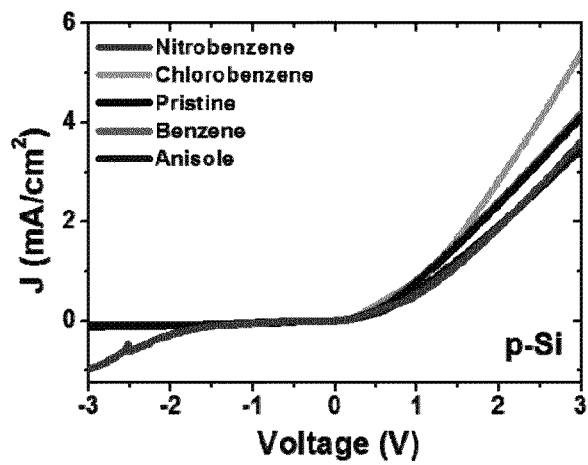
Figure 4C:
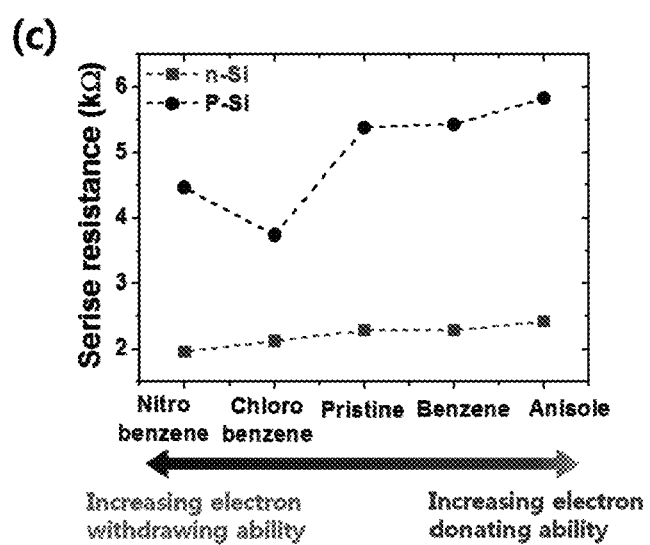

In FIG. 4 (a, b) illustrates J-V characteristics of a graphene/n-Si and p-Si SD before and after applying anisole, benzene, chlorobenzene and nitrobenzene onto the device. These aromatic molecules have an increasing electron accepting behaviour due to their electron donating groups (EDG) and electron withdrawing groups (EWG). The n-Si SD (FIG. 4 a) shows higher currents with stronger EDGs while the p-Si SD show the opposite behaviour (FIG. 4b). The response was modelled and series resistance was extracted by plots of dV/dI vs. 1/I as shown in FIG. 4(c). The $R_S$ is lowest in the presence of nitrobenzene (chlorobenzene) and highest in the anisole with n-type (p-type) silicon. The resistance increased in the EDG, whereas it decreased in the EWG, independent of the substrate type. It has to be noted that under ambient graphene usually displays p-type behaviour caused by adsorbed moisture or oxygen. Therefore, it is reasonable to assume that pristine graphene would remain in the p-doped state. Anisole electron dopes (n-doping) the graphene, increasing its sheet resistance while decreasing its work function. Conversely, nitrobenzene hole dopes (p-doping) the graphene, reducing its sheet resistance while increasing its work function. As the tendency for n-Si and p-Si diodes are the same we attribute this to the improvement in electrical conductivity of graphene in both cases.

Figure 5A:
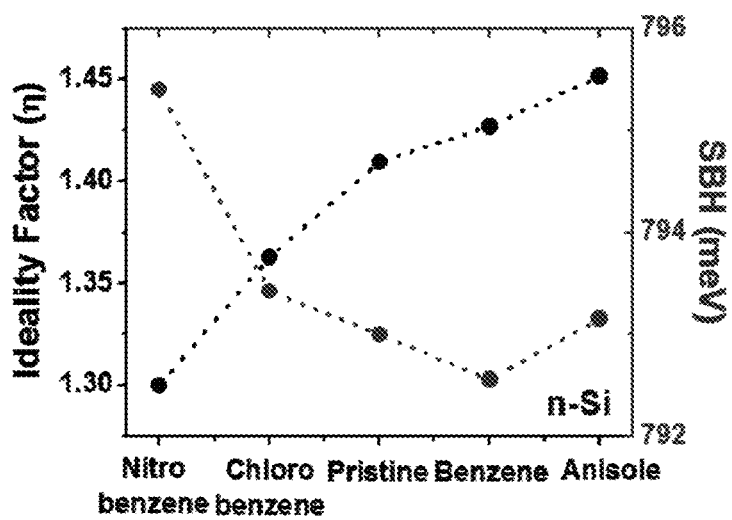
FIG. 5 illustrates experimental variation of the ideality factor η and Schottky barrier height $\phi_B$ with electron donating and withdrawing group with a graphene on (a) n-Si and (b) p-Si. (c) Schematic band diagram of the graphene/n-Si interface in the solvent with donating (anisole), reference group with no treatment and withdrawing group (nitrobenzene). The $E_{VAC}$, $E_C$, $W_G$, $\phi_B$ indicate the vacuum energy, conduction band, graphene work function, Schottky barrier height, respectively.
Figure 5B:
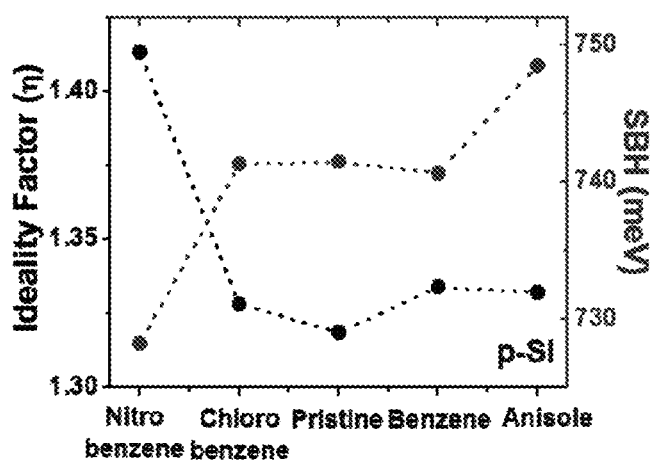

It was also demonstrated that the pristine graphene with n-Si and p-Si SD yields an ideality factor 1.41 and 1.32, respectively. As shown in FIG. 5(a), Nitrobenzene (EWG)-doped graphene/n-Si SD has improved its value to 1.3, while anisole (EDG)-doped graphene/n-Si SD is deteriorated to a value of 1.45. On the contrary to this (FIG. 4 (b)), nitrobenzene (EWG)-doped graphene/p-Si SD has deteriorated to a value of 1.41, while anisole (EDG)-doped graphene/p-Si SD has no significantly change value, contrary to expectation. FIG. 5(a), (b) also shows a plot of the experimentally determined SBH of graphene/n-Si and p-Si SD depends on EDG and EWG at room temperature.

Figure 5C:
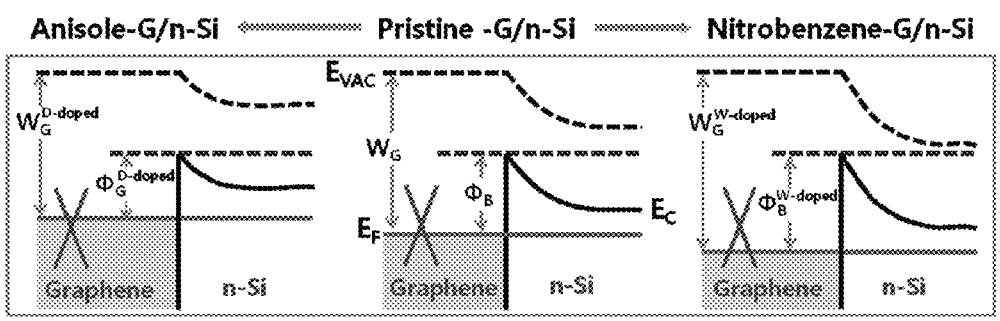

The SBH of a diode is extracted at the charge neutrality point. The SBH at the pristine graphene/n-Si interface increased from 0.79 to 0.80 eV with EWG, approximately. However, the zero bias SBH decreased from 0.73 to 0.75 eV at graphene/P—Si interface with EWG. The variation of the Schottky barrier can be explained with charge concentration difference between the pristine and the doped graphene. A schematic band diagram of the variation of SBH is depicted in FIG. 5(c). When the graphene is exposed to EDG, extra electrons are provided causing a shift of the Fermi level toward the Si conduction band. As a result, the SBH is decreased. Inversely, EWGs induce extra holes giving rise to an increase of the SBH because the Fermi level is shifted towards the valence band of Si. The change in SBH by chemically doping the graphene is small compared to gate induced doping. However it explains the obtained data perfectly and can be used for the evaluation of the doping behaviour of liquids and gases.

Figure 6A:
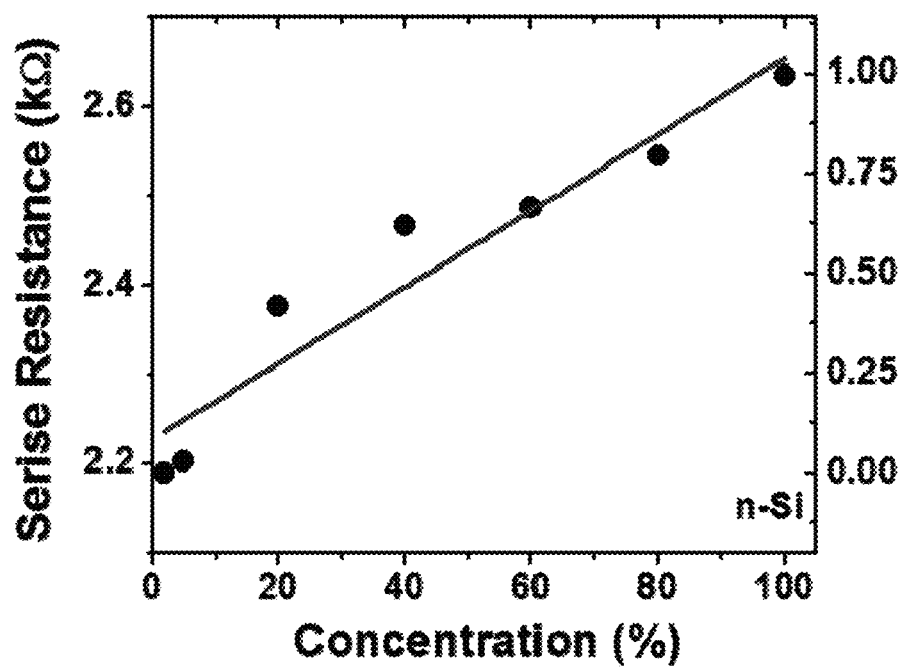
FIG. 6 illustrates (a) the $R_S$ as a function of concentration of anisole. The right y-axis shows normalized resistance. (b) Experimental variation of the ideality factor η and Schottky barrier height $\phi_B$ versus concentration.
Figure 6B:
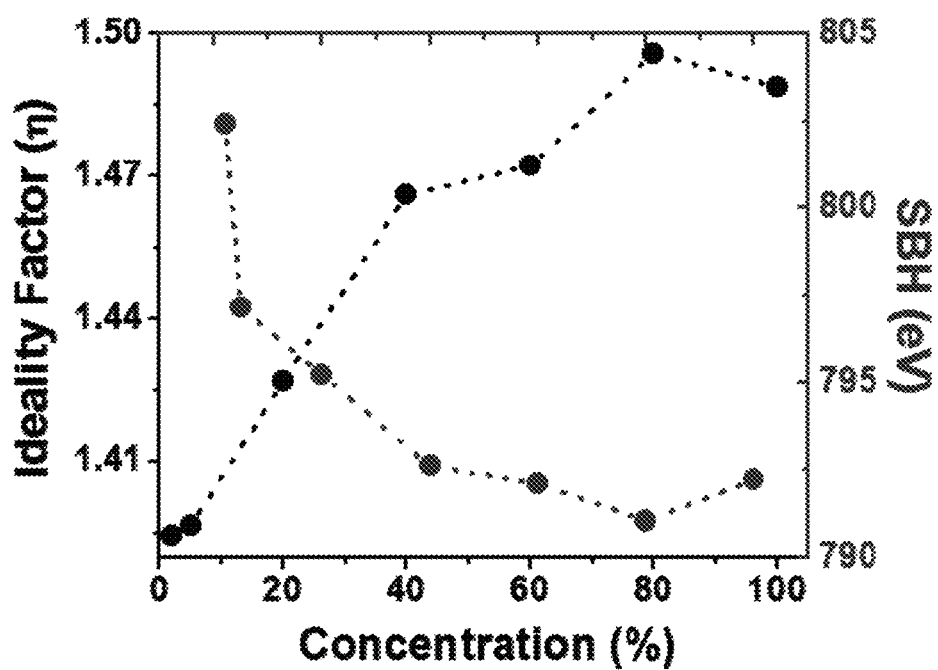

The plot of the series resistance varies depending on the concentration of anisole indicates that the relationship between anisole concentration and series resistance is increase linearly with increasing anisole concentration as shown in FIG. 6 (a). A linear relationship can be described as $$R_S = [4.27 \times n(\%) + 2227] \Omega \quad (3)$$

where n is concentration of anisole. This equation indicated that the sensitivity of graphene/n-Si device is 4.27Ω percent. The dependence of ideality factor and Schottky barrier height on concentration of anisole was also evaluated. The $\eta$ and $\phi_B$ at different concentration of anisole are plotted versus concentration in FIG. 6(b). It observed that the $\eta$ decreases with increase of concentration and the $\phi_B$ increases with concentration. The Schottky barrier height is showing an inverse behaviour to the ideality factor variation.

Moreover, the long term stability of the graphene/n-Si SD device was investigated by measurement after rinsing and baking under same condition. The resistance value was extracted at 1 V bias using diode model. The results are shown in FIG. 7 (a). It shows the resistance of a SD device changes very little during 49 days. The difference of resistance is smaller than 1.1% for the whole 49 days. Therefore, the long term stability of the device is very good. Repeatability is another important characteristic features. FIG. 7 (b) shows the high repeatability of the graphene/n-Si SD device by 24 times repeated same measuring under same condition as it mentioned before. The variation resistance is from 1% to 2% and the ideality factor also shows no significant differences during 49 days as shown in FIG. 7(c). The Raman measurement was performed to confirm about negligible degradation effect with our device.

Figure 8A:
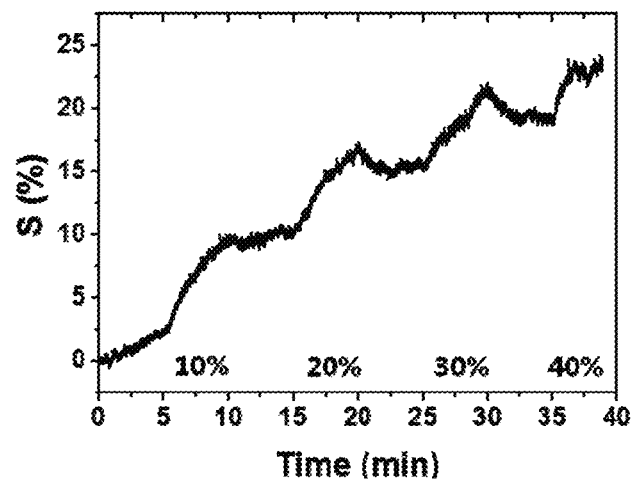
FIG. 8 illustrates (a) Sensor response of (a) CVD-transferred graphene field effect transistor (FETs) and (b) graphene/n-Si SD device depending on concentration of ammonia ($NH_3$) gas. Current as a function of time of (c) a CVD-transferred graphene FETs and (d) graphene/n-Si SDs at the concentration of $NH_3$.
Figure 8B:
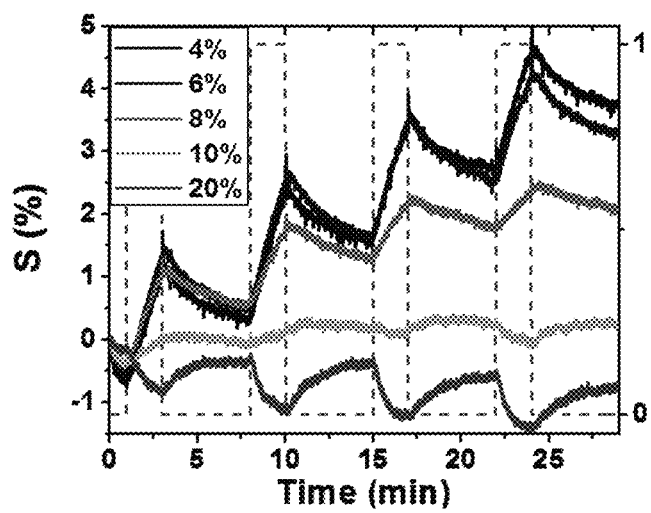
Figure 8C:
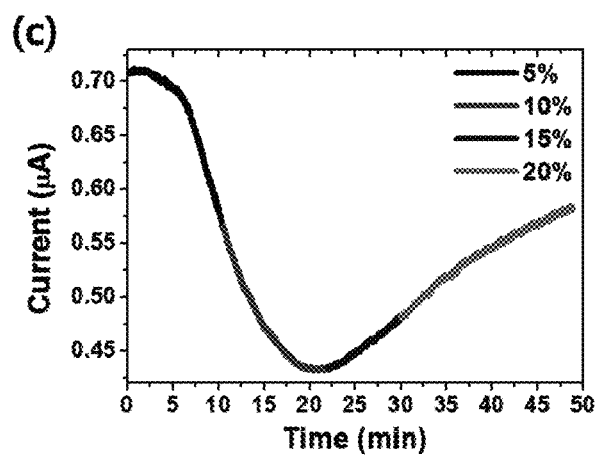
Figure 8D:
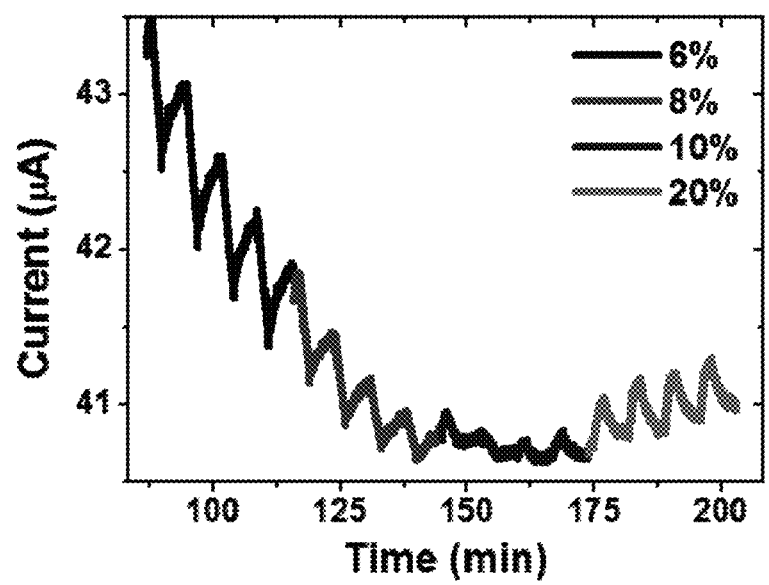

FIG. 8(a) illustrates sensor response of (a) CVD-transferred graphene field effect transistor (FETs) and (b) graphene/n-Si SD device depending on concentration of ammonia ($NH_3$) gas. Current as a function of time of (c) a CVD-transferred graphene FETs and (d) graphene/n-Si SDs at the concentration of $NH_3$.

Figure 9:
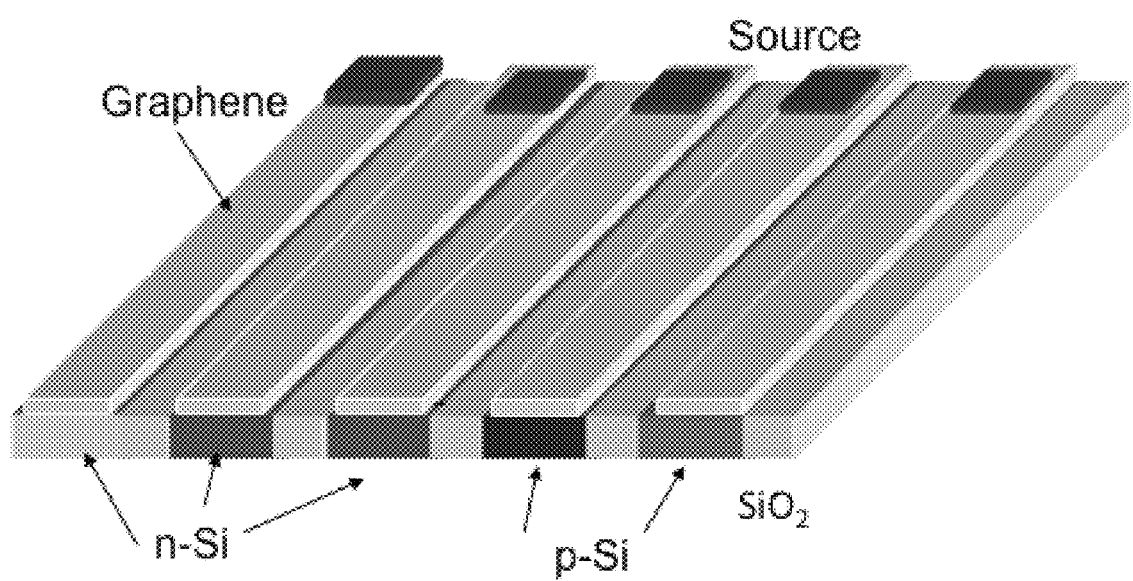
FIG. 9 illustrates a multi-functional device on a single chip with an array of sensor devices.

FIG. 9 shows a plurality of devices of the invention arranged in a sensor array. The arrays can be doped differently to produce sensor arrays with selectivity. The different doping can be done by implantation prior to the graphene deposition.

It will be appreciated that the device provides a controlled rectifying characteristics in chemically modified graphene/n-Si SD. The work function of graphene can be easily adjusted by exposure to liquid and gases treatment of electron-donor and -acceptor.

In the case of graphene/n-Si SDs doped with electron withdrawing groups (nitrobenzene), the value of ideality factor is reduced by 7.8% from 1.41 to 1.30 and series resistance also reduced 13.8% from 2.3 kΩ to 2.0 kΩ. In contrast, the value of ideality factor increased 2.8% from 1.41 to 1.45 and series resistance also increased 6.2% from 2.3 kΩ to 2.4 kΩ with electron donating groups (anisole). In the case of graphene/p-Si SDs doped with electron withdrawing groups, the value of ideality factor is increased by 7.2% from 1.32 to 1.41 and series resistance reduced 17.0% from 5.4 kΩ to 4.7 kΩ. In contrast, the value of ideality factor increased 1.0% from 1.32 to 1.33 and series resistance also increased 8.5% from 5.4 kΩ to 5.8 kΩ with electron donating groups.

It will be further appreciated that the invention shows that the electronic structure of graphene can be tailored by the chemical modification. It is considerably more simple approach and high throughput doping of graphene is possible.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A sensor device comprising:
   an electrode;
   a 2D material layer in direct contact with the electrode forming a diode, whereby exposure of the 2D material layer to an analyte changes a charge carrier density of the 2D material layer and modulates a charge transport through the diode that is capable of being sensed in a vertical direction with respect to the 2D material layer.

2. The sensor device of claim 1, wherein the 2D material layer comprises graphene.

3. The sensor device of claim 1, wherein the electrode comprises a metal or carbon and the 2D material layer comprises a semiconductor material.

4. The sensor device of claim of claim 1, wherein the electrode comprises a transition metal dichalcogenide (MoS2, WS2).

5. The sensor device of claim 1, wherein the 2D material layer includes carbon and where adsorption events on the 2D material layer modulate the charge transport through the diode to provide a sensor function.

6. The sensor device of claim 1, wherein the 2D material layer includes carbon and wherein on exposure of the 2D material layer to the analyte causes changes in a charge carrier density of the carbon such that the electrical transport of the diode is modulated.

7. The sensor device of claim 6, wherein the changes in the charge carrier density produced by a doping power of the adsorbent modulates the charge transport through the diode to provide said sensor function.

8. The sensor device of claim 1, comprising a measurement module to determine a change in a work function and a doping of the 2D material layer upon exposure to a gas, or a liquid or solid.

9. The sensor device of claim 1, wherein the analyte includes at least one of: anisole, benzene, chlorobenzene, nitrobenzene, glucose, carbon dioxide, H2S or gaseous ammonia.

10. The sensor device of claim 1, wherein exposure of the 2D material layer to the analyte causes change of charge carriers in the 2D material layer due to charge injection through an ohmic metal contact and a Schottky contact applied horizontally over an area of the 2D material layer.

11. The sensor device of claim 1, wherein the analyte includes receptors and ligands and the charge transport is modulated by receptor ligand interaction.

12. The sensor device of claim 1, wherein the analyte includes cells residing on top of a buffer layer and the charge transport is modulated by growth of cells residing on top of the buffer layer.

13. The sensor device of claim 1, wherein the 2D material layer comprises a mediation layer.

14. The sensor device of claim 1, wherein the 2D material layer comprises a dielectric or polymer mediation layer.

15. The sensor device of claim 1, wherein the 2D material layer comprises a polymer holding electrolytes mediation layer.

16. The sensor device of claim 1, wherein the 2D material layer comprises a mediation layer functionalised with at least one receptor to enable a bio-molecule sensor function.

17. The sensor device of claim 1, wherein the 2D material layer comprises a mediation layer filled with nutrition media for cells to enable the sensor function via changes of the composition of the liquid phase within the mediation layer.

18. The sensor device of claim 1, wherein the electrode comprises a n- or p-doped silicon substrates.

19. The sensor device of claim 1, wherein the 2D material layer is exposed to gas or liquid or an analyte.

20. A bottom contacted 2D-layer device comprising the sensor device of claim 1.

21. A photosensor comprising the sensor device of claim 1.

22. A sensor array comprising a plurality of devices, wherein at least one device comprises the sensor device of claim 1.

* * * * *